(12) United States Patent
Furuta et al.

(10) Patent No.: US 8,729,321 B2
(45) Date of Patent: May 20, 2014

(54) FLUOROALKYL IODIDE AND ITS PRODUCTION PROCESS

(75) Inventors: Shoji Furuta, Yokohama (JP); Yusuke Sugahara, Kashima-gun (JP); Keiko Nakase, Ichihara (JP); Keisuke Mori, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 1006 days.

(21) Appl. No.: 11/406,289

(22) Filed: Apr. 19, 2006

(65) Prior Publication Data

US 2007/0249876 A1  Oct. 25, 2007

(30) Foreign Application Priority Data

Apr. 20, 2005 (JP) ................... 2005-122286

(51) Int. Cl.
*C07C 17/00* (2006.01)
(52) U.S. Cl.
USPC ............ 570/171; 570/172; 570/175; 570/134
(58) Field of Classification Search
USPC .................................. 570/171, 172, 175, 134
See application file for complete search history.

(56) References Cited

U.S. PATENT DOCUMENTS

| 3,226,449 | A | 12/1965 | Blanchard et al. | |
| 5,068,471 | A * | 11/1991 | Paul et al. | 570/139 |
| 5,929,292 | A | 7/1999 | Shimoyama | |
| 6,720,371 | B2 | 4/2004 | Furuta et al. | |
| 6,919,490 | B2 * | 7/2005 | Funakoshi et al. | 570/172 |
| 2005/0004337 | A1 | 1/2005 | Furuta et al. | |

FOREIGN PATENT DOCUMENTS

| EP | 1 380 557 A1 | 1/2004 |
| JP | 5-255146 | 10/1993 |
| JP | 6-206908 | 7/1994 |
| JP | 6-305995 | 11/1994 |
| JP | 8-252453 | 10/1996 |
| JP | 10-59880 | 3/1998 |
| JP | 2002-316957 | 10/2002 |
| WO | WO 02/062735 A1 | 8/2002 |

OTHER PUBLICATIONS

U.S. Appl. No. 12/212,716, filed Sep. 18, 2008, Furuta, et al.
Qing-Yun Chen, et al., "Copper-Induced Telomerization of Tetrafluoroethylene with Fluoroalkyl Iodides", Journal of Fluorine Chemistry, vol. 36, XP-002953551, 1987, pp. 483-489.
Office Action issued Mar. 1, 2011 in corresponding JP Application No. 2005-122286.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A process for producing a fluoroalkyl iodide as a telomer $R^f(CF_2CF_2)_nI$ (wherein $R^f$ is a $C_{1-10}$ fluoroalkyl group, and n is an integer of from 1 to 6) by telomerization from a fluoroalkyl iodide represented by the formula $R^fI$ (wherein $R^f$ is as defined above) as a telogen and tetrafluoroethylene ($CF_2CF_2$) as a taxogen, which comprises a liquid phase telomerization step of supplying a homogeneous liquid mixture of the telogen and the taxogen from the lower portion of a tubular reactor, moving the mixture from the lower portion towards the upper portion of the reactor in the presence of a radical initiator over a retention time of at least 5 minutes while the reaction system is kept in a liquid phase state is under conditions where no gas-liquid separation will take place, so that the taxogen supplied to the reactor is substantially consumed by the reaction in the reactor, and drawing the reaction product from the upper portion of the reactor.

22 Claims, 1 Drawing Sheet

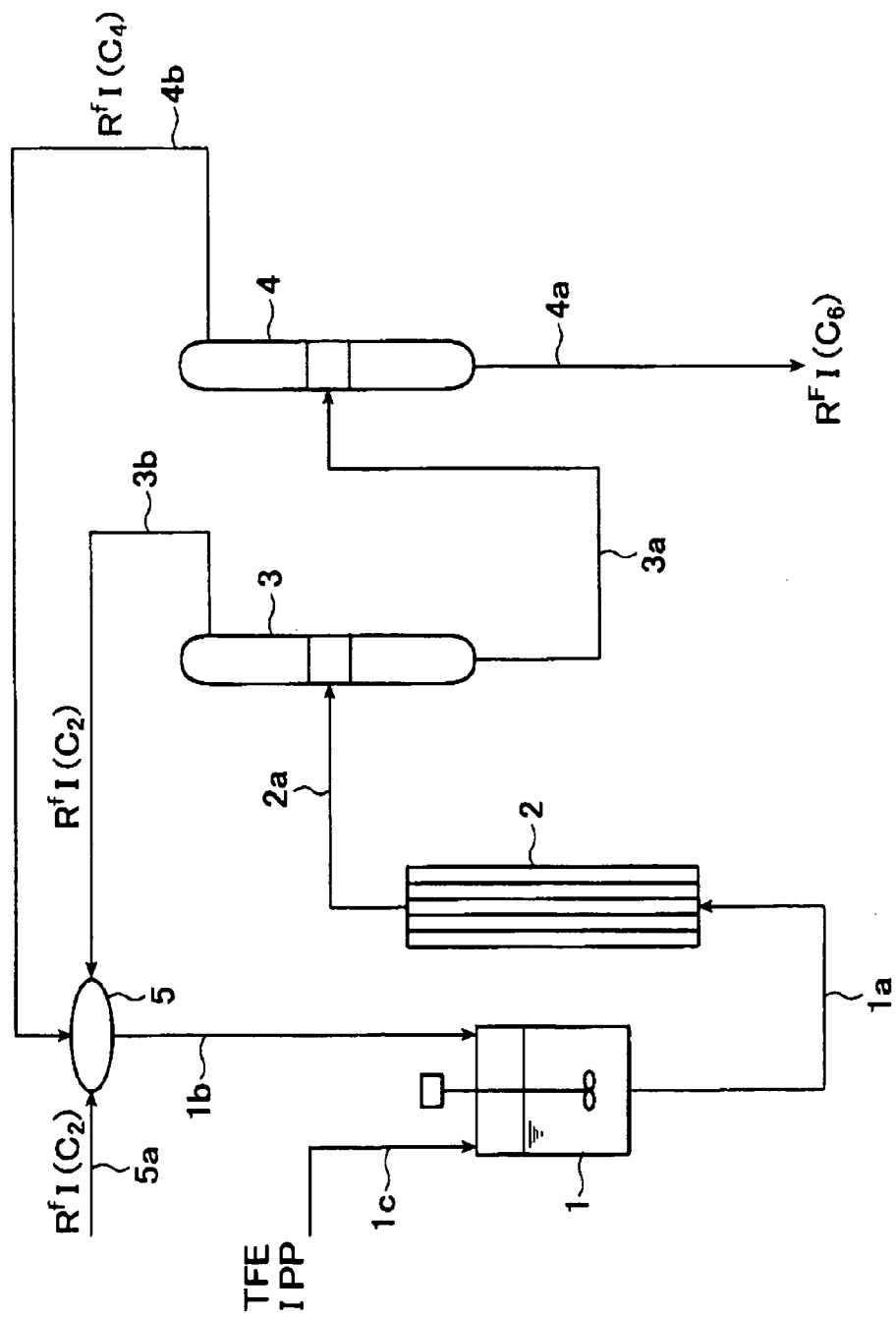

FLUOROALKYL IODIDE AND ITS PRODUCTION PROCESS

The present invention relates to a process for producing a fluoroalkyl iodide by telomerization and a fluoroalkyl iodide.

A fluoroalkyl iodide (hereinafter sometimes referred to as $R^F I$) is useful as a material for synthesis of a fluoroalkyl acrylate constituting a water repellent and oil repellent latex, a material for synthesis of a fluorinated surfactant, etc. In the fluoroalkyl iodide, the carbon chain length of $R^F$ desired to obtain water repellency and oil repellency is usually C4 or longer, depending upon the purpose of use. For production of $R^F I$ having such a carbon chain length, chain length elongation by addition of a taxogen employing a short chain $R^F I$ as a telogen i.e. telomerization is utilized. As the taxogen, usually tetrafluoroethylene $CF_2CF_2$ (hereinafter sometimes referred to as TFE) is used, and thus a telomer fluoroalkyl iodide $R^F I$ is obtained as $R^F(CF_2CF_2)_n I$ (n is the degree of polymerization). The starting material telogen $R^F I$ is typically $C_2F_5I$, which is synthesized from tetrafluoroethylene, $IF_5$ and $I_2$.

By simply carrying out the telomerization, a 1:1 addition product of a telogen and a taxogen mainly forms, and only a very small amount of a telomer having a chain length more highly elongated will be obtained. It has been known that the efficiency of formation of C6-12 $R^F I$ will be increased by use of a free radical generating catalyst such as a peroxide for the telomerization (for example, U.S. Pat. No. 3,226,449). The publication also discloses use of a telogen mixture of $C_2F_5I$ and $C_4F_9I$. The reaction in this publication is a liquid phase reaction conducted in one step.

In addition to the telomerization by means of free radical generation, telomerization by a catalytic reaction utilizing the redox system and telomerization by thermal reaction have been known as telomerization by which a telomer having an elongated chain length can be obtained. At present, long chain telomers longer than C14 are hardly utilized, and their formation are not substantially required. Thus, formation of a telomer having a narrow distribution in a specific chain length range or a telomer having a single chain length has been required to obtain desired characteristics. However, in each of the above method, selectivity for a single chain length tends to be low, control of the chain length is difficult, and a telomer mixture having a broad chain length distribution will be obtained.

It has been known that in the thermal reaction of reacting a telogen and a taxogen in a vapor phase, the proportion of formation of a long chain telomer longer than C14 can be reduced by increasing the ratio of telogen/taxogen. In order to reduce the proportion of formation of a long chain telomer in the vapor phase reaction, a continuous process of dividedly supplying the taxogen TFE from an inlet of a tubular reactor and from another portion, has been proposed (for example, JP-A-5-255146). This publication also discloses that the chain length distribution can be narrowed when telomers having chain lengths of C4 and C6 which are sequentially formed are used as the telogen together with the C2 starting material, as compared with a case where the C2 starting material alone is used as the telogen.

Further, it has been proposed that in the above thermal telomerization in the vapor phase, a telomer having a chain length shorter than the final chain length is recycled to a predetermined zone of the reactor so as to improve the selectivity for the carbon chain length (for example, JP-A-6-305995).

According to the above vapor phase telomerization, a fluoroalkyl iodide telomer having a relatively narrow chain length distribution can be obtain, but the telomerization has to be carried out under extremely restricted conditions with regard to e.g. introduction of the material taxogen or the recycled telomer to the reactor. Further, due to the vapor phase reaction, there is such a problem that a perfluoroalkyl compound forms as an impurity by coupling of fluoroalkyl radicals to be generated during the reaction.

On the other hand, a liquid phase reaction employing a catalyst is advantageous in view of energy since the reaction temperature is inherently low as compared with the above vapor phase reaction, and is advantageous in that a thermally unstable taxogen (TFE) is less likely to be decomposed. JP-A-6-206908 discloses a process wherein the liquid phase reaction is carried out in a slender cylindrical reaction space, the reaction mixture which left the cylindrical reaction space is separated, and a telomer having the reaction progressed is drawn, and on the other hand, a telomer having no desired chain length and an unreacted material are recycled to the initial stage of the reaction system. The publication discloses that the proportion of formation of C8 and longer telomers can be improved. Further, the waste gas can be reduced by the recycle.

Further, WO02/062735 proposes a process by a liquid phase reaction which comprises separating the reaction mixture of the initial material telogen and TFE into three fractions, and subjecting a second fraction having a degree of polymerization of TFE lower by 1 than the desired degree of polymerization to reaction in a second reactor. In this process, a telomer mixture having at least a desired degree of polymerization is obtained by a two-step reaction. No special reactor is required for each of the two reactors, and the reactor is an autoclave or the like.

The above telomerization by means of a liquid phase method is advantageous over a vapor phase method in view of operation and energy, and in that no impurities such as a perfluoroalkyl compound will be formed as by-products. By the telomerization by means of a liquid phase method, a telomer having a desired chain length or longer will be obtained, but it tends to be difficult to control the chain length, and particularly it tends to be difficult to suppress formation of a telomer having a chain longer than the desired chain length. Even when a known reaction method is applied so as to control the chain length, a telomer having a broad chain length distribution will be obtained in fact. Further, in continuous operation, a telomer having the chain length controlled will be obtained by removing an unreacted product from the reaction product as far as possible, but such remarkably decreases the reaction efficiency. As mentioned above, it is difficult to obtain a fluoroalkyl iodide telomer having a narrow chain length distribution in a desired range, particularly a fluoroalkyl iodide telomer having an aimed single carbon chain length with high production efficiency, by a telomerization process by means of a liquid phase method.

Under these circumstances, the present inventors have conducted extensive studies on a process for producing a fluoroalkyl iodide by means of liquid phase telomerization, by which the chain length can be controlled while the production amount is maintained, and by which a fluoroalkyl iodide having a desired carbon chain length particularly a single carbon chain length can be obtained with high yield and with high production efficiency. As a result, they have achieved a process wherein particularly a tubular reactor is used as a reactor, reaction materials telogen and taxogen (TFE) are preliminarily formed into a homogeneous liquid mixture, which is supplied to the tubular reactor, and the taxogen supplied to the reactor is substantially consumed in the reactor while the reaction system is kept in a liquid phase state under conditions where no gas-liquid separation will take place. According to this process, TFE which has been discharged out of the system of the process, as a gas component from an unreacted material which is drawn from the reactor and recycled to the reaction system, can be utilized with a high material efficiency. Further, they have further found that according to this process, by preliminarily forming the reaction materials into a homogeneous liquid mixture i.e. a mixture containing TFE at a concentration not to exceed the saturated concentration in the liquid telogen (molar ratio of telogen/taxogen being higher than 1), and supplying it to the tubular reactor, a telomer having a narrow chain length distribution, particularly a telomer having a desired single carbon chain length, can be obtained with an extremely high selectivity and productivity, and the above object will be achieved. The present invention has been accomplished on the basis of this discovery.

The process for producing a fluoroalkyl iodide of the present invention is a process for producing a fluoroalkyl iodide as a telomer $R^f(CF_2CF_2)_nI$ (wherein $R^f$ is a $C_{1-10}$ fluoroalkyl group, and n is an integer of from 1 to 6) by telomerization from a fluoroalkyl iodide represented by the formula $R^fI$ (wherein $R^f$ is as defined above) as a telogen and tetrafluoroethylene ($CF_2CF_2$) as a taxogen, which comprises a liquid phase telomerization step of supplying a homogeneous liquid mixture of the telogen and the taxogen from the lower portion of a tubular reactor, moving the mixture from the lower portion towards the upper portion of the reactor in the presence of a radical initiator over a retention time of at least 5 minutes while the reaction system is kept in a liquid phase state, so that the taxogen supplied to the reactor is substantially consumed by the reaction in the reactor, and drawing the reaction product from the upper portion of the reactor.

BRIEF DESCRIPTION OF THE DRAWINGS

FIG. 1 is a process flowchart illustrating a preferred embodiment of the present invention.

Now, the present invention will be described in detail with reference to the preferred embodiments.

In the present invention, as described above, a tubular reactor is used and the reaction is carried out while the reaction system is kept in a liquid phase state. Therefore, tetrafluoroethylene (TFE) supplied to the reaction system can be in contact with a telogen $R^fI$ without gas-liquid separation and is thereby consumed in the reaction system with high efficiency, and thus no or only a very small amount of tetrafluoroethylene is contained in the reaction product drawn from the reactor.

In the present invention, the tubular reactor is one having a ratio of length/maximum inner diameter of at least 1, preferably one having said ratio of at least 3.

The cross-section of the tubular reactor to be used in the present invention is not limited to circular, and it may be elliptic or rectangular. The maximum inner diameter of the tubular reactor is usually from 0.5 mm to 1.5 m. As the tubular reactor, hollow fibers may also be used. The hollow fibers may have an inner diameter smaller than the above inner diameter, and for example, carbon nanofibers having a fiber diameter less than 1 μm may be utilized.

The tubular reactor may comprise a single tube or a plurality of tubes.

The retention time of the reaction system in the tubular reactor is preferably set so that TFE supplied to the reaction system sufficiently contributes to the reaction and is consumed. Specifically, the retention time is at least 5 minutes, preferably at least 10 minutes, more preferably at least 15 minutes, most preferably at least 30 minutes. In a case where a mixing tank and a distillation column mentioned hereinafter are provided respectively at stages before and after the tubular reactor, the retention time includes the retention time in a line (tubular transport line) from the outlet of the mixing tank to the inlet of the distillation column so long as the liquid mixture of the reaction materials contains a radical initiator.

In conventional liquid phase telomerization employing e.g. an autoclave having mixing function as a reactor, the retention time in a line to introduction of the reaction product drawn from the lower portion of the reactor to the distillation column is regularly less than 5 minutes, and is usually at a level of from 2 to 3 minutes.

The tubular reactor is not necessarily vertically installed, and it may be installed, for example, at a slant, so long as the material supply opening is provided at the lower portion preferably at the bottom of the reactor, the reaction product drawing opening is provided at the upper portion preferably at the top of the reactor, and the reaction mixture can be moved from the lower portion towards the upper portion of the reactor while the reaction system is kept in a liquid stated phase without gas-liquid separation.

In the tubular reactor, the reaction temperature and the reaction pressure are not particularly limited so long as the reaction system supplied in a liquid state can be kept in a liquid phase state. The reaction temperature is preferably such that the internal temperature of the tubular reactor is usually from 40 to 100° C. The internal temperature of the tubular reactor is preferably the same or lower than the temperature at which the liquid mixture is prepared, for example the internal temperature of the mixing tank. The reaction pressure is preferably from 0.3 to 1.5 MPa as the pressure at the inlet of the tubular reactor.

The starting material telogen $R^fI$ may be selected from fluoroalkyl iodides having a $C_{1-10}$ fluoroalkyl group depending upon the aimed carbon chain length of the telomer $R^{F}I$. In the reaction system of the present invention, in a case where a simple reaction of a material telogen $R^fI$ and taxogen is assumed, it is essentially preferred to supply a telogen $R^fI$ having carbon atoms smaller than those of an aimed telomer $R^FI$ to the reaction system. For example, in a case where an aimed telomer $R^FI$ is $C_6F_{13}I$, a preferred reaction material telogen to be supplied to the reaction system is $C_4F_9I$.

In a case where such a reaction system is carried out by means of a continuous process comprising a step of recycling an unreacted material to the reaction system as mentioned hereinafter, it is preferred to use $C_2F_5I$ as the initial material telogen. Namely, $C_4F_9I$ consumed as the reaction material in the reaction system for formation of aimed $C_6F_{13}I$, is supplied by telomerization of the coexisting initial material $C_2F_5I$ to $C_4F_9I$. Thus, in a continuous process for production of $C_6F_{13}I$ comprising a step of recycling an unreacted material, a telogen mixture of the reaction material $C_4F_9I$ and the initial reaction material $C_2F_5I$ can be supplied to the reaction system. Thus, the longer the carbon chain length of the aimed telomer $R^FI$, the more different varieties of materials the telogen mixture contains.

In the present invention, a homogeneous liquid mixture of a telogen and a taxogen is supplied to the tubular reactor. Specifically, the homogeneous liquid mixture of a telogen $R^fI$ and a taxogen TFE to be supplied to the reaction system, may be prepared by dissolving the taxogen in the liquid telogen at most at a saturated concentration. The material ratio of $R^fI$ to TFE varies depending upon an aimed telomer, but the molar ratio of $R^fI$/TFE is preferably higher than 1, that is, a mixture rich in $R^fI$ is preferred. Since TFE will not be dissolved in the liquid $R^fI$ in an equimolar amount or more, the molar ratio of $R^fI$/TFE would not be smaller than 1 in the liquid mixture having TFE dissolved in the liquid $R^fI$ at most at a saturated concentration. The saturated concentration of TFE varies depending upon $R^fI$. For example, in a case where an aimed telomer is $C_6R^fI$ ($C_6F_{13}I$), the molar ratio of $R^fI$/TFE in the liquid mixture of reaction materials is preferably from 20 to 200. The material $R^fI$ may be a mixture of $C_4F_9I$ and $C_2F_5I$.

The radical initiator is not particularly limited so long as telomerization of a fluoroalkyl iodide by means of tetrafluoroethylene can be carried out in a liquid phase, and it may be preferably a general purpose peroxide type compound or an azo type compound depending upon the reaction temperature.

The peroxide type compound may, for example, be a peroxyketal, a diacyl peroxide, a peroxydicarbonate, a peroxyester, a hydroperoxide, a dialkyl peroxide, a ketone peroxide or an inorganic peroxide.

The peroxyketal may, for example, be 1,1-bis(t-butylperoxy)-3,3,5-trimethylcyclohexane, 1,1-bis(t-butylperoxy)cyclohexane, n-butyl-4,4-bis(t-butylperoxy)pentanoate, 2,2-bis(t-butylperoxy)butane, 1,1-bis(t-hexylperoxy)-3,3,5-trimethylcyclohexane, 1,1-bis(t-hexylperoxy)cyclohexane, 1,1-bis(t-hexylperoxy)cyclododecane or 2,2-bis(4,4-di-t-butylperoxycyclohexyl)propane.

The diacyl peroxide may, for example, be perfluorobutanoyl peroxide, isobutyl peroxide, lauroyl peroxide, 3,5,5-trimethylhexanoyl peroxide, succinic acid peroxide, benzoyl peroxide, octanoyl peroxide or stearoyl peroxide.

The peroxydicarbonate may, for example, be diisopropyl peroxydicarbonate (sometimes referred to as IPP), di-2-ethylhexyl peroxydicarbonate, di-n-propyl peroxydicarbonate, di-2-ethoxyethyl peroxydicarbonate, di-3-methoxybutyl peroxydicarbonate or bis(4-t-butylcyclohexyl)peroxydicarbonate.

The peroxyester may, for example, be 1,1,3,3-tetramethylbutyl peroxyneodecanoate, t-hexyl peroxyneodecanoate, t-butyl peroxyneodecanoate, t-hexyl peroxypivalate, t-butyl peroxypivalate, 1,1,3,3-tetramethylbutylperoxy-2-ethylhexanoate, t-hexylperoxy-2-ethylhexanoate, t-butylperoxy-2-ethylhexanoate, t-butylperoxyisobutylate, t-butylperoxylaurate, t-butylperoxy-3,5,5-trimethylhexanoate, t-hexyl peroxyisopropylmonocarbonate, t-butyl peroxyisopropylcarbonate, 2,5-dimethyl-2,5-bis(benzoylperoxy)hexane, t-butyl peroxyacetate or bis-1-butyl peroxyisophthalate.

The hydroperoxide may, for example, be p-menthane hydroperoxide, diisopropylbenzene hydroperoxide, 1,1,3,3-tetramethylbutyl hydroperoxide, cumene hydroperoxide or t-butyl hydroperoxide.

The dialkyl peroxide may, for example, be α,α'-bis(t-butylperoxy)diisopropylbenzene, dicumyl peroxide, 2,5-dimethyl-2,5-bis(t-butylperoxy)hexane, t-butyl cumyl peroxide, di-t-butylperoxide or 2,5-dimethyl-2,5-bis(t-butylperoxy)hexyne-3.

The ketone peroxide may, for example, be methyl ethyl ketone peroxide, cyclohexanone peroxide, methylcyclohexanone peroxide, methyl acetoacetate peroxide or acetylacetone peroxide.

The inorganic peroxide may, for example, be preferably ammonium persulfate or potassium persulfate.

The azo type compound may, for example, be preferably an azonitrile, an azo compound, an azoamide or an azoamidine.

The azonitrile may, for example, be azobisisobutyronitrile, 2,2'-azobis(4-methoxy-2,4-dimethylvaleronitrile), 2,2'-azobis(2,4-dimethylvaleronitrile), 2,2'-azobis(2-methylpropionitrile), 2,2'-azobis(2-methylbutyronitrile), 1,1'-azobis(cyclohexane-1-carbonitrile) or 1-[1-cyano-1-methylethylazo]formamide(2-(carbamoylazo)isobutyronitrile).

The azo compound may, for example, be dimethyl-2,2'-azobisisobutyrate, azobiscyanovaleric acid, dimethyl-2,2'-azobis(2-methylpropionate) or 4,4'-azobis(4-cyanopentanoic acid).

The azoamide may, for example, be 2,2'-azobis{2-methyl-N-[1,1-bis(hydroxymethyl)-2-hydroxyethyl]propioamide}, 2,2'-azobis{2-methyl-N-[2-(1-hydroxybutyl)]-propioamide}, 2,2'-azobis[2-methyl-N-[2-hydroxyethyl]-propioamide], 2,2'-azobis[N-(2-propenyl)-2-methylpropioamide] or 2,2'-azobis[N-[2-(2-imidazolin-2-yl)propane].

The azoamidine may, for example, be 2,2'-azobis(2-methylpropioamidine) or 2,2'-azobis[N-(2-hydroxyethyl)-2-methyl-propioamidine].

The above radical initiator may be supplied to the reaction system in an amount equivalent to preferably from 0.01 to 2 mol %, more preferably from 0.1 to 1 mol %, based on the reaction materials. Such a radical initiator may be used in the form of a diluted solution in the material telogen, a hydrocarbon type organic solvent or a fluorinated organic solvent.

The homogeneous liquid mixture to be supplied to the tubular reactor may be obtained by dissolving the taxogen $CF_2CF_2$ in a liquid phase state telogen $R^fI$ at most at a saturated concentration. Such a homogeneous liquid mixture may be prepared by any means such as stirring or circulation so long as the mixture is homogeneous. For example, it may be prepared in a mixing tank located upstream of the tubular reactor. Such an embodiment is included in the present invention. Namely, the process for producing a fluoroalkyl iodide of the present invention may further comprise a step of preparing a homogeneous liquid mixture of at least the above telogen and taxogen in a mixing tank located upstream of the tubular reactor.

The mixing tank is not particularly limited so long as a homogeneous liquid mixture can be prepared. For example, an autoclave having stirring function may be preferably used. The radical initiator may be supplied to the mixing tank, or it may be preliminarily incorporated in the liquid mixture to be prepared in the mixing tank by circulation from the reaction system. Mixing may be carried out at a temperature of from 0 to 100° C., preferably from 30 to 80° C.

In the present invention, it is preferred that the retention time in the mixing tank is short and the retention time in the tubular reactor is long. Specifically, in the present invention, the retention time in the mixing tank is preferably at most 30 minutes, more preferably at most 15 minutes. Typically, it is set at a level of from 5 to 15 minutes. In a conventional process, the mixing tank may be employed as a continuous system tank reactor (CSTR) in some cases. In such a case, the reaction time (retention time) in the reactor is so long as about 100 minutes. When the line connected to the reactor is considered as one type of a tubular reactor, the retention time in the line is less than 5 minutes and is overwhelmingly short as compared with the retention time in the reactor at a stage before the line.

In the present invention, in a case where a radical initiator is present in the mixing tank, the reaction takes place also in the mixing tank, but the reaction time (retention time) in the mixing tank is very short as compared with the conventional reaction time.

As a preferred embodiment of the present invention, an embodiment may be mentioned wherein the retention time in the tubular reactor is longer than the retention time in the mixing tank. A specific embodiment is such that the retention time in the mixing tank is at a level of from 5 to 15 minutes and the retention time in the tubular reactor is at least 30 minutes.

The reaction product drawn from the tubular reactor contains a telomer having a desired carbon chain length with a narrow distribution, particularly a telomer having a single carbon chain length with a high selectivity. In the present invention, separation and purification of the desired telomer from the reaction product by distillation, or separation of the telomer having a single carbon chain length by distillation, can be carried out. Accordingly, the process for producing a fluoroalkyl iodide according to the present invention may further comprise a distillation step of distilling a fraction of at least a fluoroalkyl iodide having a desired carbon chain length from the reaction product drawn from the upper portion of the reactor.

Further, more preferably the process further comprises, in the above distillation step, a step of separating a fraction of a fluoroalkyl iodide having a chain length shorter than the desired carbon chain length and recycling it to the upstream portion of the reaction system. For distillation, known apparatus and method may suitably be used. The fraction to be recycled usually contains the unreacted material $R^fI$ contained in the reaction product and a very small amount of remaining TFE.

The above distillation step may comprise a single stage or two or more stages.

In the present invention, each of the above steps is carried out preferably in continuous operation. Particularly, the respective steps are connected and carried out continuously.

In the present invention as described above, a fluoroalkyl iodide $R^FI$ having a total carbon chain length of C3 or longer can be obtained as a telomer $R^f(CF_2CF_2)_nI$ (wherein $R^f$ is a $C_{1-10}$ fluoroalkyl group, and n is an integer of from 1 to 6). The desired total carbon chain length of the telomer $R^FI$ is usually at a level of C22 at longest. In the present invention, it is preferred to selectively produce particularly one of telomers having carbon chain lengths of C4, C6 and C8 among such $R^FI$. According to the above process of the present invention, high selectivity of a fluoroalkyl iodide having a desired carbon chain length can be achieved. For example, in a case where it is desired to produce a fluoroalkyl iodide having a carbon chain length of C6, formation of telomers having carbon chain lengths longer than C6 can be suppressed, specifically, a ratio of C8/C6 in the fluoroalkyl iodide composition of at most 10% at the outlet of the tubular reactor can be achieved.

Accordingly, the present invention further provides a fluoroalkyl iodide $R^FI$ having a narrow carbon chain length distribution or having a single carbon chain length to be obtained as the telomer.

The fluoroalkyl iodide $R^FI$ having the above carbon chain length to be obtained as the telomer is useful, for example, as a material of an alcohol component of a fluoroalkyl acrylate. For this application, particularly C6 to C12 $R^FI$ ($C_6F_{13}I$ to $C_{12}F_{25}I$) are useful, and particularly, C6 $R^FI$ ($C_6F_{13}I$) has such advantages that water repellency can be imparted while the feeling of a substrate is maintained, it has favorable adhesive properties to a substrate at low temperature (low temperature curing properties) and favorable emulsification stability at the time of polymerization will be achieved. Further, fluoroalkyl compounds having carbon chain lengths of at most C6 are preferred also in view of environmental compatibility such as biodegradability.

Production of an fluoroalkyl acrylate employing a fluoroalkyl iodide $R^FI$ as a preparation material may be carried out by any know process of employing $R^FI$, and in such a case, $R^FI$ to be obtained in the present invention may be used. For example, as a fluoroalkyl acrylate employing $R^FI$ as a preparation material, $CH_2=CZCOO(C_2H_4)_nR^F$ (wherein Z is —H, —$CH_3$, —$C_2H_5$, —Cl, —F or —Br), preferably $CH_2=CZCOOC_2H_4R^F$ may be mentioned.

To obtain the ester, usually, first, (1) ethylene is added to $R^FI$, followed by (2) esterification. A method for esterification (2) may be a first method of carrying out esterification with a (meth)acrylic acid compound (such as a metal salt), or a second method of carrying out alcohol synthesis and esterification in this order.

The above steps may be carried out in accordance with a known method. The first method including the ethylene addition step (1) may be carried out, for example, in accordance with a method as disclosed in JP-A-2002-62735, and the description of the ethylene addition reaction in the publication is incorporated herein by reference.

The alcohol synthesis in the second esterification method may be carried out in accordance with the following reaction:

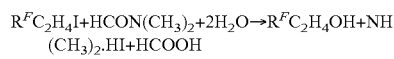

$R^FC_2H_4I+HCON(CH_3)_2+2H_2O \rightarrow R^FC_2H_4OH+NH(CH_3)_2.HI+HCOOH$

A fluoroalkyl acrylate can be obtained by the reaction of the above obtained alcohol $R^FC_2H_4OH$ with an acrylic acid $CH_2=CZCOOH$ (wherein Z is as defined above).

In the present specification, the term acrylic generically includes compounds with different substituents Z in the above acryloyl $CH_2=CZCOO—$ (such as methacrylic, ethacrylic and halogenated acrylic).

The above obtained fluoroalkyl acrylate is useful, for example, as a polymerization material of a latex. Needless to say, in emulsion polymerization for production of a latex, another copolymerizable monomer such as vinyl chloride can be used.

In the present invention, the process for producing a fluoroalkyl iodide by the telomerization, a process for producing a fluoroalkyl acrylate employing $R^FI$ as a preparation material and further, a process for producing a latex, may be connected and carried out in a sequential process.

According to the present invention as described above, telomerization can be conducted with a high material utilization rate. Particularly by effective consumption of TFE, the amount of gas purged from the reaction product can be reduced, whereby the environmental load can be reduced and further, $R^fI$ accompanying the purged gas is also reduced, whereby the iodine recovery rate will also improve.

Further, according to the present invention, a fluoroalkyl iodide having a chain length controlled can be obtained, whereby a fluoroalkyl iodide having a desired chain length can be obtained with high efficiency.

FIG. 1 is a process flowchart simply illustrating a preferred embodiment of the process for producing a fluoroalkyl iodide according to the present invention. FIG. 1 illustrates an embodiment of a continuous operation process employing a mixing tank 1, a tubular reactor 2, a distillation column 3 and a distillation column 4. This embodiment is merely one example to describe the present invention, and the present invention is by no means restricted to this embodiment. In the following, explanation is made with reference to an example wherein IPP is used as the radical initiator and $C_6F_{13}I$ is to be produced as an aimed telomer $R^FI$.

In FIG. 1, the mixing tank 1 is, for example, an autoclave having stirring function. The material taxogen (TFE) is introduced to the mixing tank 1 from an upper line 1c, and the starting material telogen $R^fI$ (C2) supplied to a line 5a is introduced to the mixing tank 1 from a line 1b by means of a mixer 5. The interior of the mixing tank 1 is heated with stirring to prepare a homogeneous liquid mixture having TFE dissolved in $R^fI$, and a solution having IPP diluted with the telogen is introduced from the line 1c to the mixing tank 1. The prepared liquid in the reaction system is drawn from the bottom of the mixing tank 1 by means of a line 1*a* and introduced to the bottom of the tubular reactor 2.

The tubular reactor 2 is, for example, a reactor having a plurality of tubes disposed in parallel, and the reaction system supplied from the bottom is dividedly supplied to the respective tubes and moves towards the upper portion in the respective tubes over a predetermined retention time. Then, the reaction product drawn from the top of the tubular reactor 2 is introduced to the first distillation column 3 by means of a line 2*a*.

In the distillation column 3, the reaction product is separated into a fraction containing an unreacted material $R^FI$ (C2) and a fraction of $R^FI$ having a chain length of C4 or longer, and the fraction containing $R^FI$ (C2) drawn from a line 3*b* is recycled to the mixing tank 1 from the line 1*b* by means of the mixer 5. The fraction of $R^FI$ having a chain length of C4 or longer is introduced to the second distillation column 4 by means of a line 3*a*. In the distillation column 4, the fraction is separated into a C4 fraction and a fraction of $R^FI$ having a chain length of C6 or longer, and the C4 fraction drawn from a line 4*b* is recycled to the mixing tank 1 from the line 1*b* by means of the mixer 5. The fraction of $R^FI$ having a chain length of C6 or longer is drawn from a line 4*a* as an aimed telomer $R^FI$.

EXAMPLES

Now, the present invention will be explained in further detail with reference to Examples and Comparative Example wherein $C_6F_{13}I$ is to be produced. However, the present invention is by no means restricted to such specific Examples.

In the following, assuming a material system to be supplied to a reactor in stable operation of a continuous process (for example, FIG. 1) of recycling an unreacted material, a telogen material mixture was used.

Example 1

In a 1 L autoclave made of hastelloy equipped with a stirrer and an insertion tube, as a mixing tank, $C_2F_5I$ (800 g) and $C_4F_9I$ (200 g) were charged as fluoroalkyl iodides $R^FI$, and heated at an the internal temperature of 77° C. with stirring.

The heated mixture was supplied from the insertion tube of the autoclave to a jacketed tubular reactor (single tube) made of stainless steel having a sectional area of 19.6 cm² and an internal volume of 1,840 mL at a flow rate of 3.6 L/hr and at the same time, $C_2F_5I$ at a flow rate of 2.88 L/hr, $C_4F_9I$ at a flow rate of 0.72 L/hr and tetrafluoroethylene ($C_2F_4$:TFE) at a flow rate of 0.045 kg/hr were supplied to the autoclave (molar ratio of $R^FI$/TFE=61.3).

After the internal temperature of the tubular reactor was stabilized at 65° C., a 50 w % diluted solution (solvent: $C_2F_5I$:$C_4F_9I$=4:1 mass ratio) of diisopropyl peroxydicarbonate (IPP) as a radical initiator was continuously added to the autoclave at 0.1 kg/hr. After stable operation for about 2 hours, samples were taken out from the outlet of the tubular reactor and their compositions were analyzed by gas chromatography. By the gas chromatography analysis, it was confirmed that TFE was consumed in the tubular reactor. The results are shown in Table 1.

Example 2

The same operation as in Example 1 was carried out except that the internal temperature in the tubular reactor was 70° C. The compositions were analyzed in the same manner as in Example 1 and as a result, it was confirmed that TFE was consumed in the tubular reactor. The results are shown in Table 1.

Comparative Example 1

Into a 500 mL autoclave made of hastelloy equipped with a stirrer and an insertion tube, $C_2F_5I$ (128 kg) and $C_4F_9I$ (32 kg) were charged as fluoroalkyl iodides $R^FI$, and heated at an internal temperature of 77° C. with stirring.

After the internal temperature of the autoclave was stabilized at 77° C., $C_2F_5I$ at a flow rate of 113.8 L/hr, $C_4F_9I$ at a flow rate of 28.5 L/hr, TFE at a flow rate of 1.79 kg/hr and the same radical initiator (50 w % diluted solution of IPP) as in Example 1 at a flow rate of 2.0 kg/hr were continuously added to the autoclave and reacted. The reaction product was supplied to a pressure resistant container having an internal volume of 200 L cooled with dry ice at a flow rate of 142.3 L/hr to terminate the reaction.

After stable operation for about 1 hour, samples were taken out from the outlet of the autoclave and their compositions were analyzed.

TABLE 1

|  |  | Ex. 1 | Ex. 2 | Comp. Ex. 1 |
|---|---|---|---|---|
| Liquid phase volume (L) | Autoclave | 0.5 | 0.5 | 80 |
|  | Tubular reactor | 1.34 | 1.34 | — |
| Internal temperature (° C.) | Autoclave | 77 | 77 | 77 |
|  | Tubular reactor | 65 | 70 | — |
| Material flow rate (L/hr) | $C_2F_5I$ | 2.88 | 2.88 | 113.8 |
|  | $C_4F_9I$ | 0.72 | 0.72 | 28.5 |
|  | Total $R^FI$ | 3.6 | 3.6 | 142.3 |
| Retention time (min) | Autoclave | 8.3 | 8.3 | 33.7 |
|  | Tubular reactor | 30.7 | 30.7 | — |
| TFE analyzed value at the outlet of the reactor |  | N.D. | N.D. | 0.73% |
| Formation rate ($C_8F_{17}I$/$C_6F_{13}I$) % |  | 6.9 | 7.9 | 12.3 |

N.D.: at most 0.05%

As described above, it is understood that in Examples of the present invention, TFE is not detected at the outlet of the reaction system and is substantially consumed in the reaction system. Even though the amount of TFE remaining at the outlet of the reaction system in Examples is 0.05% (limit of detection), it is at most one-tenth the amount (0.73%) of TFE remaining at the outlet of the reaction system in Comparative Example. In Examples and Comparative Example, the TFE concentration (theoretical value) in the material system is calculated assuming that all TFE supplied to the autoclave is dissolved in a liquid phase.

The entire disclosure of Japanese Patent Application No. 2005-122286 filed on Apr. 20, 2005 including specification, claims, drawings and summary are incorporated herein by reference in its entirety.

What is claimed is:

1. A process for producing a $C_6F_{13}I$ fluoroalkyl iodide telomer, comprising:
 telomerizing tetrafluoroethylene ($CF_2CF_2$) taxogen with a fluoroalkyl iodide telogen $R^FI$ selected from the group consisting of $C_2F_5I$, $C_4F_9I$, and mixtures thereof, as a liquid phase mixture, in which the molar ratio of $R^FI$/TFE in the liquid phase mixture is from 20 to 200, by supplying a homogeneous liquid mixture of the telogen and the taxogen into the lower portion of a vertically aligned tubular reactor;

moving the reaction mixture from the lower portion of the reactor towards the upper portion of the reactor in the presence of a peroxide or azo radical initiator over a retention time of at least 10 minutes while the reaction system in the reactor is kept in the liquid phase state under conditions such that no gas-liquid separation takes place and the taxogen supplied to the reactor is substantially consumed by the reaction in the reactor; and withdrawing the reaction product from the upper portion of the reactor;

where the internal temperature of the tubular reactor is kept at a temperature of 40 to 100° C., no more than 0.05% TFE taxogen remains in the reaction product withdrawn from the upper portion of the reactor, the concentration of the taxogen dissolved in the liquid telogen in said homogeneous liquid mixture does not exceed the saturated concentration in the liquid telogen, and the ratio of $C_8F_{17}I/C_6F_{13}I$ in the reaction product at the outlet of the tubular reactor is at most 10%.

2. The process for producing a $C_6F_{13}I$ fluoroalkyl iodide according to claim 1, wherein the reaction product withdrawn from the upper portion of the reactor is not recycled.

3. The process for producing a $C_6F_{13}I$ fluoroalkyl iodide according to claim 1, which further comprises preparing the homogeneous liquid mixture of at least the telogen and the taxogen in a mixing tank located upstream of the tubular reactor.

4. The process for producing a $C_6F_{13}I$ fluoroalkyl iodide according to claim 1, which further comprises distilling at least a fraction of a fluoroalkyl iodide having the desired carbon chain length from the reaction product that is withdrawn from the upper portion of the reactor.

5. The process for producing a $C_6F_{13}I$ fluoroalkyl iodide according to claim 4, which further comprises, in said distillation of at least a fraction of a fluoroalkyl iodide, separating a fraction of a fluoroalkyl iodide having a chain length shorter than the desired carbon chain length and recycling it to the upstream portion of the reaction system.

6. The process for producing a $C_6F_{13}I$ fluoroalkyl iodide according to claim 1, wherein each of the steps of the process is conducted in continuous operation.

7. The process for producing a $C_6F_{13}I$ fluoroalkyl iodide according to claim 1, wherein the peroxide radical initiator is a peroxyketal, a diacylperoxide, a peroxydicarbonate, a peroxyester, a hydroperoxide, a dialkyl peroxide, a ketone peroxide or an inorganic peroxide and the azo radical initiator is an azonitrile, an azo compound, an azoamide or an azoamidine.

8. The process for producing a $C_6F_{13}I$ fluoroalkyl iodide according to claim 7, wherein the peroxyketal is 1,1-bis(t-butylperoxy)-3,3,5-trimethylcyclohexane, 1,1-bis(t-butylperoxy)cyclohexane, n-butyl-4,4-bis(t-butylperoxy)pentanoate, 2,2-bis(t-butylperoxy)butane, 1,1-bis(t-hexylperoxy)-3,3,5-trimethylcyclohexane, 1,1-bis(t-hexylperoxy)cyclohexane, 1,1-bis(t-hexylperoxy)cyclododecane or 2,2-bis(4,4-di-t-butylperoxycyclohexyl)propane.

9. The process for producing a $C_6F_{13}I$ fluoroalkyl iodide according to claim 7, wherein the diacyl peroxide is perfluorobutanoyl peroxide, isobutyl peroxide, lauroyl peroxide, 3,5,5-trimethylhexanoyl peroxide, succinic acid peroxide, benzoyl peroxide, octanoyl peroxide or stearoyl peroxide.

10. The process for producing a $C_6F_{13}I$ fluoroalkyl iodide according to claim 7, wherein the peroxydicarbonate is diisopropyl peroxydicarbonate, di-2-ethylhexyl peroxydicarbonate, di-n-propyl peroxydicarbonate, di-2-ethoxyethyl peroxydicarbonate, di-3-methoxybutyl peroxydicarbonate or bis(4-t-butylcyclohexyl)peroxydicarbonate.

11. The process for producing a $C_6F_{13}I$ fluoroalkyl iodide according to claim 7, wherein the peroxyester is 1,1,3,3-tetramethylbutyl peroxyneodecanoate, t-hexyl peroxyneodecanoate, t-butyl peroxyneodecanoate, t-hexyl peroxypivalate, t-butyl peroxypivalate, 1,1,3,3-tetramethylbutylperoxy-2-ethylhexanoate, t-hexylperoxy-2-ethylhexanoate, t-butylperoxy-2-ethylhexanoate, t-butylperoxyisobutylate, t-butylperoxylaurate, t-butylperoxy-3,5,5-trimethylhexanoate, t-hexyl peroxyisopropylmonocarbonate, t-butyl peroxyisopropylcarbonate, 2,5-dimethyl-2,5-bis(benzoylperoxy)hexane, t-butyl peroxyacetate or bis-1-butyl peroxyisophthalate.

12. The process for producing a $C_6F_{13}I$ fluoroalkyl iodide according to claim 7, wherein the hydroperoxide is p-menthane hydroperoxide, diisopropylbenzene hydroperoxide, 1,1,3,3-tetramethylbutyl hydroperoxide, cumene hydroperoxide or t-butyl hydroperoxide.

13. The process for producing a $C_6F_{13}I$ fluoroalkyl iodide according to claim 7, wherein the dialkyl peroxide is α,α'-bis(t-butylperoxy)diisopropylbenzene, dicumyl peroxide, 2,5-dimethyl-2,5-bis(t-butylperoxy)hexane, t-butyl cumyl peroxide, di-t-butylperoxide or 2,5-dimethyl-2,5-bis(t-butylperoxy)hexyne-3.

14. The process for producing a $C_6F_{13}I$ fluoroalkyl iodide according to claim 7, wherein the ketone peroxide is methyl ethyl ketone peroxide, cyclohexanone peroxide, methylcyclohexanone peroxide, methyl acetoacetate peroxide or acetylacetone peroxide.

15. The process for producing a $C_6F_{13}I$ fluoroalkyl iodide according to claim 7, wherein the azonitrile is azobisisobutyronitrile, 2,2'-azobis(4-methoxy-2,4-dimethylvaleronitrile), 2,2'-azobis(2,4-dimethylvaleronitrile), 2,2'-azobis(2-methylpropionitrile), 2,2'-azobis(2-methylbutyronitrile), 1,1'-azobis(cyclohexane-1-carbonitrile) or 1-[1-cyano-1-methylethylazo]formamide(2-(carbamoylazo)isobutyronitrile).

16. The process for producing a $C_6F_{13}I$ fluoroalkyl iodide according to claim 7, wherein the azo compound is dimethyl-2,2'-azobisisobutyrate, azobiscyanovaleric acid, dimethyl-2,2'-azobis(2-methylpropionate) or 4,4'-azobis(4-cyanopentanoic acid).

17. The process for producing a $C_6F_{13}I$ fluoroalkyl iodide according to claim 7, wherein the azoamide is 2,2'-azobis{2-methyl-N-[1,1-bis(hydroxymethyl)-2-hydroxyethyl]propioamide}, 2,2'-azobis{2-methyl-N-[2-(1-hydroxybutyl)]-propioamide}, 2,2'-azobis[2-methyl-N-[2-hydroxyethyl]-propioamide], 2,2'-azobis[N-(2-propenyl)-2-methylpropioamide] or 2,2'-azobis[N12-(2-imidazolin-2-yl)propane].

18. The process for producing a $C_6F_{13}I$ fluoroalkyl iodide according to claim 7, wherein the azoamidine is 2,2'-azobis(2-methylpropioamidine) or 2,2'-azobis[N-(2-hydroxyethyl)-2-methyl-propioamidine].

19. The process for producing a $C_6F_{13}I$ fluoroalkyl iodide according to claim 3, wherein the retention time in the mixing tank ranges from 5 to 15 minutes, and the retention time in the tubular reactor is at least 30 minutes.

20. The process for producing a $C_6F_{13}I$ fluoroalkyl iodide according to claim 3, wherein the radical initiator is supplied to the reaction system in an amount ranging from 0.01 to 2 mol % based on the reaction materials.

21. The process for producing a $C_6F_{13}I$ fluoroalkyl iodide according to claim 1, wherein the retention time of the reaction mixture in the reactor is at least 15 minutes.

22. The process for producing a $C_6F_{13}I$ fluoroalkyl iodide according to claim 1, wherein the retention time of the reaction mixture in the reactor is at least 30 minutes.

* * * * *